United States Patent [19]

Cage et al.

[11] 4,198,957
[45] * Apr. 22, 1980

[54] METHOD OF USING AN ELECTRICALLY HEATED SURGICAL CUTTING INSTRUMENT

[75] Inventors: John M. Cage, Los Altos, Calif.; Robert F. Shaw, 2316 Leavenworth St., San Francisco, Calif. 94100; Paul E. Stoft, Menlo Park, Calif.

[73] Assignee: Robert F. Shaw, San Francisco, Calif.

[ * ] Notice: The portion of the term of this patent subsequent to May 16, 1995, has been disclaimed.

[21] Appl. No.: 780,031

[22] Filed: Mar. 22, 1977

Related U.S. Application Data

[60] Division of Ser. No. 534,756, Dec. 2, 1974, Pat. No. 4,089,336, which is a continuation of Ser. No. 63,645, Aug. 13, 1970, abandoned, which is a continuation of Ser. No. 681,737, Nov. 9, 1967, abandoned.

[51] Int. Cl.$^2$ ............................................. A61B 17/32
[52] U.S. Cl. ...................................... 128/1 R; 30/140; 128/303.1; 219/241
[58] Field of Search ................ 128/303 R, 1 R, 303.1, 128/303.13, 303.14, 404–406; 30/140; 219/233, 251, 210, 239, 227–231, 512, 505, 520, 240, 241, 235–238, 499, 504

[56] References Cited

U.S. PATENT DOCUMENTS

| | | | |
|---|---|---|---|
| Re. 26,276 | 10/1967 | Hirschhorn | 128/303.1 |
| 956,604 | 5/1910 | Savoy | 219/233 X |
| 958,753 | 5/1910 | Meyer | 128/303.14 X |
| 1,083,386 | 1/1914 | Chapman | 30/140 |
| 1,713,970 | 5/1929 | Lowry et al. | 128/303.14 |
| 1,735,271 | 11/1929 | Groff | 128/303.14 |
| 1,794,296 | 2/1931 | Hyams | 128/303.14 |
| 1,930,214 | 10/1933 | Wappler | 128/303.14 |
| 2,012,938 | 9/1935 | Beuoy | 128/303.14 |
| 2,623,977 | 12/1952 | Weiskopf | 30/140 |
| 2,763,762 | 9/1956 | Jepson | 128/303.1 X |
| 2,795,697 | 6/1957 | Nagel | 219/499 X |
| 2,917,614 | 12/1959 | Caliri et al. | 128/303.1 X |
| 3,207,159 | 9/1965 | Tateisi | 128/303.1 |
| 3,234,356 | 2/1966 | Babb | 128/303.1 |
| 3,502,080 | 3/1970 | Hirschhorn | 128/303.1 |
| 3,526,750 | 9/1970 | Siegel | 219/233 |
| 4,089,336 | 5/1978 | Cage et al. | 128/303.1 |

FOREIGN PATENT DOCUMENTS

| | | | |
|---|---|---|---|
| 550456 | 10/1956 | Italy | 30/140 |
| 605328 | 7/1948 | United Kingdom | 30/140 |
| 615027 | 12/1948 | United Kingdom | 30/140 |
| 641034 | 8/1950 | United Kingdom | 128/303.14 |

Primary Examiner—Robert W. Michell
Assistant Examiner—Michael H. Thaler
Attorney, Agent, or Firm—Lyon & Lyon

[57] ABSTRACT

A surgical cutting instrument includes an electrically heated cutting edge and an automatic control system for maintaining the cutting edge at a constant high temperature for sterilizing the blade, cutting tissue, and cauterizing the incised tissue to reduce hemorrhage from the cut surfaces of the tissues (hemostasis).

1 Claim, 3 Drawing Figures

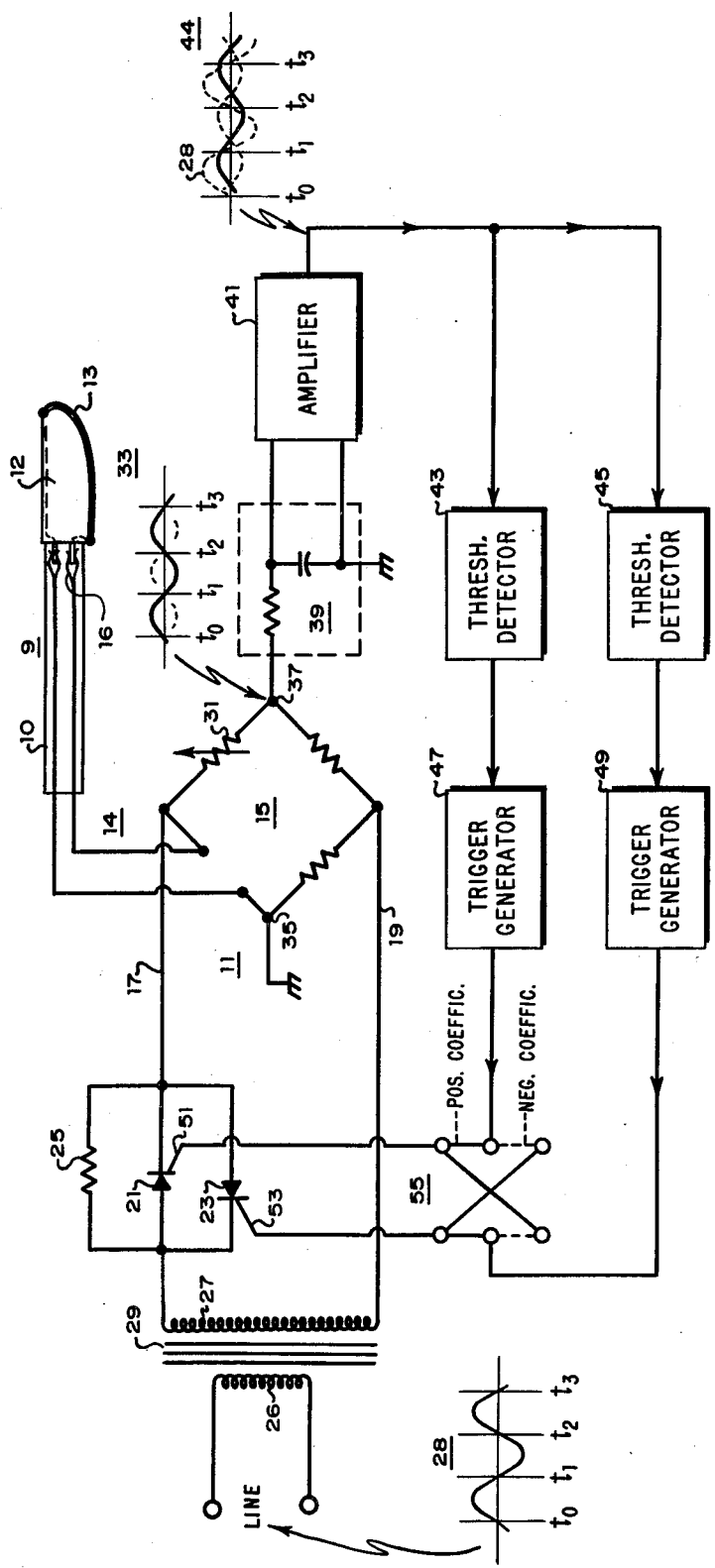
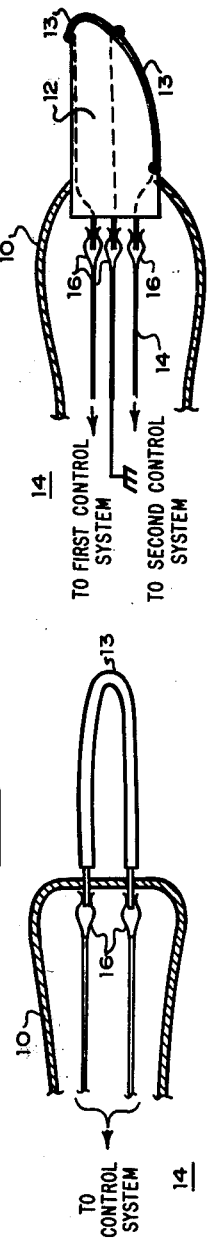

METHOD OF USING AN ELECTRICALLY HEATED SURGICAL CUTTING INSTRUMENT

RELATED APPLICATIONS

This application is a divisional of U.S. patent application Ser. No. 534,756 filed Dec. 2, 1974, now U.S. Pat. No. 4,089,336 which is a continuation of U.S. patent application Ser. No. 63,645 filed Aug. 13, 1970, now abandoned, which is a continuation of U.S. patent application Ser. No. 681,737 filed Nov. 9, 1967, now abandoned.

BACKGROUND OF THE INVENTION

The control of bleeding during surgery accounts for a major portion of the total time involved in an operation. The bleeding that occurs when tissue is incised obscures the surgeon's vision, reduces his precision and often dictates slow and elaborate procedures in surgical operations. Each bleeding vessel must be grasped in pincer-like clamps to stop the flow of blood and the tissue and vessel within each clamp must then be tied with pieces of fine thread. These ligated masses of tissue die and decompose and thus tend to retard healing and promote infection.

SUMMARY OF THE INVENTION

Accordingly, the present invention provides a surgical cutting instrument having a cutting edge which is electrically heated to a constant high temperature for sterilizing the blade, cutting the tissue and cauterizing the surfaces of the incision, thereby allowing surgery to be more rapidly performed. This is accomplished in accordance with the illustrated embodiment of this invention by providing an electrically heated element disposed as the cutting edges of the blade and by providing a control system which maintains the cutting edge at a high substantially constant temperature during its use. The hot cutting edge according to the present invention decreases the amount of tissue that is damaged and reduces the tendency of the instrument to stick to the heated tissue in the incision. The material used in the electrically heated cutting edge has a negative temperature coefficient of resistance to insure that electrical power applied to the cutting edge is dissipated primarily in the regions thereof which tend to be cooled by contact with tissue. The temperature at which the cutting edge of the blade is maintained depends upon such factors as the nature of the tissue to be cut, the speed of cutting desired, the degree of tissue coagulation desired, and the non-adherence of the blade to the incised tissue and generally is maintained between 300°-1000° C. for typical incisions. The instantaneous temperature of the cutting edge is monitored by measuring the resistance of the heating element itself or through the use of thermocouple elements disposed in the blade near the cutting edge, and the monitoring signal thus derived controls the power applied to the heating element. The handle of the cutting instrument is thermally insulated from the blade to permit comfortable use of the instrument and the handle and blade with its electrically heated cutting edge are detachable for easy replacement and interchangeability with blade, scoops and cutting edges of various shapes and sizes determined by the nature of the incision to be made and the tissue to be cut.

DESCRIPTION OF THE DRAWING

FIG. 1 is a schematic diagram showing the cutting instrument and the temperature control system therefor, according to the preferred embodiment of the present invention, and FIGS. 2 and 3 are pictorial views of other embodiments of cutting instruments according to the present invention for use with circuitry as shown in FIG. 1.

DESCRIPTION OF THE PREFERRED EMBODIMENT

Referring now to FIG. 1 of the drawing, there is shown the surgical cutting instrument 9 connected to a temperature-measuring and power-controlling system 11. The cutting instrument 9 includes a thin ceramic card 12 in the desired shape of a surgical cutting blade which is detachable from the handle or holder 10. An electrically heated element 13 is disposed along the leading edge of the card 12 to form its cutting edge and is electrically connected to the control circuit through the cable 14 and the connectors 16. The element 13 may be a single filament attached to the edge of the card 12, for example, using conventional ceramic welding materials or may be a layer of electrically conductive material vapor-deposited along the edge of the card 12. Also, the heating element 13 may have sufficient cross-sectional area to be self-supporting, as shown in FIG. 2, so that the blade 18 is formed entirely by the element 13 alone. The material used in the element 13 ideally should have a negative temperature coefficient of resistance so that as selected portions of the element cool when in contact with tissue, the resistance of such portions will increase and thereby localize the portions of the element 13 in which additional power supplied by the control system will be dissipated. The temperature of the element may thus be maintained substantially constant over the entire length thereof as portions of the element 13 contact tissue. Suitable materials having negative temperature coefficient of resistance include silicon carbide, carbon, boron silicate and such semiconductor materials as silicon and germanium. Of course, material having a positive coefficient of resistance may also be used. However, when materials of this type are used, care should be taken to shape the element 13 so that substantially the entire length of the element 13 contacts tissue in use. This is required to prevent the additional power supplied by the control system 11 from being dissipated in the portions of the element which do not cool when in contact with tissue and, hence, which have higher resistance than the cooler portions. For cutting applications where it is not convenient to shape the element 13 so that its entire length is in contact with tissue each time it is used, the element 13 may consist of a plurality of electrically isolated elements 13 and 13', as shown in FIG. 3, with each of the elements 13 and 13' connected to a separate temperature measuring and power-controlling system of the type shown in FIG. 1.

The resistance of the element 13 is included in a bridge circuit 15 which is connected to receive alternating signal appearing on lines 17 and 19. The level of alternating signal appearing on lines 17 and 19 and, hence, the power applied to element 13 is determined by the conduction angles of the controlled rectifiers 21 and 23 which are connected in conduction opposition in parallel across the series resistor 25. Power is supplied to the control system 11 through the primary and secondary windings 26 and 27 of power input transformer 29. Alternating line signal 28 applied to the transformer 29 is stepped down typically to about 24 volts for the safety of the patient and the surgeon and the average current flow per half cycle of the alternating signal is determined in part by the series resistor 25 and by the conduction angle of a silicon-controlled rectifier 21, 23.

The operating temperature of the element 13 may be determined by adjusting one of the resistors, say resistor 31, in the bridge circuit 15. Any variation in the operating temperature of element 13 from a set value unbalances the bridge 15 and produces a control signal 33 across the diagonal terminals 35, 37 of the bridge circuit 15 which is either in phase or out of phase with the applied line signal, depending upon whether the operating temperature of the element is above or below the set value of operating temperature. A phase-shifting network 39 is connected to the output terminals of the bridge circuit 15 for applying the error signal 44 with respect to ground to the input of error amplifier 41 with a small amount of phase shift relative to the applied line signal 28. This provides control of the conduction angle of the controlled rectifiers 21, 23 over a greater portion of a half cycle of the applied line signal. The output of amplifier 41 is applied to the threshold detectors 43, 45 which respond to the amplified error signal attaining selected values slightly above and below zero. The threshold detectors 47 and 49 thus activate the trigger pulse generators 47 and 49 at the proper times in alternate half cycles of applied line signal 28 to apply conduction-initiating pulses to the gate electrodes 51, 53 of the controlled rectifiers 21, 23. Thus, increased conduction angle of the controlled rectifiers 21 and 23 increases the power applied to the element 13 to maintain the element at a preselected operating temperature as the element tends to cool down in contact with skin tissue. However, if the operating temperature of the element 13 should exceed the set value due, for example, to thermal overshoot upon removal of the element 13 from contact with skin tissue, the phase of the error signal 33 with respect to the applied line signal reverses. This causes the trigger pulse generators to supply conduction-initiating pulses to the gate electrodes of the controlled rectifiers 21, 23 during alternate half cycles when these rectifiers are back biased. This causes a decrease in the power delivered to the element 13 with a concomitant drop in its operating temperature to about the set value of operating temperature. When this occurs, the proper phase relationship between error signal and line signal is restored and power is again supplied to the element 13. Conversion of the control system 11 for operation with elements 13 having negative or positive temperature coefficients of resistance merely requires that the trigger pulses from the generators 47 and 49 be applied through reversing switch 55 to the proper controlled rectifier 21, 23 during the forward-biasing half cycle of line signal 28.

It should be apparent that other temperature control systems may also be used to maintain the operating temperature of the element 13 substantially constant at a preselected value. For example, a thermocouple sensor may be disposed on the card 12 in close proximity with the element 13 or a thermocouple element may even be formed on element 13 using another material or dissimilar work function to form the thermocouple junction. The signal from such thermocouple may then be used to control the operating temperature of the element 13 by controlling the power supplied thereto.

We claim:
1. A method of hemostatic cutting using a blade means having a cutting edge operating at an elevated temperature, the method comprising:
heating the cutting edge by conducting an electrical current in a conduction path along the cutting edge including a conductive means having a negative temperature coefficient of resistance; and
self regulating the heating of the cutting edge by increasing the electrical resistance of those portions of the electrical conduction path that are cooled.

* * * * *